United States Patent [19]

Wong et al.

[11] Patent Number: 4,533,740

[45] Date of Patent: Aug. 6, 1985

[54] β-LACTONE PROCESS

[75] Inventors: P. K. Wong, Katy; Mark K. Dickson, Houston, both of Tex.

[73] Assignee: Shell Oil Company, Houston, Tex.

[21] Appl. No.: 609,604

[22] Filed: May 14, 1984

[51] Int. Cl.³ ................... C07D 305/14; C07D 305/12
[52] U.S. Cl. .................................................. 549/328
[58] Field of Search ........................................ 549/328

[56] References Cited

FOREIGN PATENT DOCUMENTS 1066572 10/1959 Fed. Rep. of Germany ...... 549/295

OTHER PUBLICATIONS

Mark A. Andrews et al., J. Am. Chem. Soc. (1981), vol. 103, pp. 2894–2896.
Mark A. Andrews et al., J. Am. Chem. Soc. (1982), vol. 104, pp. 4268–4270.

Primary Examiner—Norma S. Milestone

[57] ABSTRACT

This invention relates to a process for converting an olefin to a β-lactone using a palladium catalyst.

2 Claims, No Drawings

β-LACTONE PROCESS

FIELD OF THE INVENTION

This invention relates to a process for converting olefins to β-lactones utilizing a palladium catalyst and carbon monoxide.

BACKGROUND OF THE INVENTION

The lactones are useful as intermediates in synthesis, as solvents, as drugs and in perfumery and flavorings. A direct route of converting readily available olefin feed stocks such as higher olefins, cyclopentadiene and isobutylene to the corresponding β-lactones would provide a desirable process for converting lower value feedstocks to higher value products that would be particularly useful in the detergent and polymer areas.

SUMMARY OF THE INVENTION

This invention relates to a process for converting olefins to β-lactones. This process comprises first reacting the olefin with a bis(organonitrile)chloronitropalladium (II) complex in an organic aprotic solvent, then reacting the reaction product of olefin and the palladium complex with carbon monoxide in an aprotic solvent and then separating a β-lactone product from the reaction mixture.

DESCRIPTION OF THE PREFERRED EMBODIMENTS

This invention relates to a process for converting an olefin of the general formula

$$R_1R_2C = CR_3R_4 \qquad (I)$$

to the corresponding β-lactones of the general formula

wherein $R_1$, $R_2$, $R_3$ and $R_4$ individually are hydrogen or alkyl of up to 20 carbon atoms or two or more of the R groups are combined to form a (cyclic) alkylene group which process comprises reacting said olefin with a bis(organonitrile)chloropalladium (II) catalyst, and reacting the reaction product of the olefin and the catalyst with carbon monoxide. The resulting product will be one or a mixture of isomers of β-lactone (II and/or III). Isomer distribution will be determined primarily by the steric configuration of the olefin. In olefins wherein the substituents at $R_3$ and $R_4$ are sterically bulky compared to the substituents at $R_1$ and $R_2$, the process will be more selective to III than to II.

It is postulated that the reaction process proceeds as follows

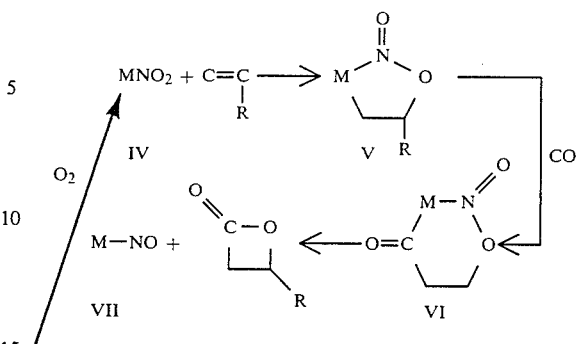

The catalyst IV, which is a metallonitro complex, reacts with the olefin to produce a metallocycle V. The metallocycle reaction product is then reacted with carbon monoxide to produce an intermediate carbonyl-metallocycle VI which then decomposes to the desired β-lactone and a metallonitrosyl complex VII. The β-lactone can be removed from the reaction product by traditional means and utilized as desired. It is further possible to remove the metallonitrosyl compound and oxidize it back to the original metallonitro compound. Thus, a nitro-nitrosyl redox cycle can be used to regenerate the bis(organonitrile)chloropalladium (II) complex. In general, the above reaction process is carried out sequentially, i.e., the catalyst and olefin are reacted to produce the metallocycle, which is then reacted with carbon monoxide to produce the β-lactone. However, depending on reactivity of the olefin, the above reaction sequence can be carried simultaneously, i.e., the catalyst, olefin and carbon monoxide can be placed in the reaction vessel at the same time, although the reaction will proceed through the sequence described above. A relatively high reactivity of the olefin is required to minimize side reactions with increased by-product formation or ineffective use of catalyst, resulting in lower yields of β-lactone.

The olefins utilized in the instant process are defined by (I) above and typically have carbon numbers ranging from 2 to about 40. They may comprise polycyclic olefins such as norbornene, substituted norbornenes, norbornadienes, etc., or they may comprise substituted or unsubstituted cyclic olefins such as cyclopentene or cyclohexene, or they may comprise branched olefins such as isoprene and isobutylene, or they may comprise linear olefins, internal or alpha, such as 1-dodecene, 2-butene, etc.

The catalyst comprises a bis(organonitrile)chloronitropalladium (II) complex. The organonitrile ligand can be any readily available nitrile, R-CN, where R is alkyl, aryl, alkaryl or aralkyl. Suitable examples are acetonitrile, propionitrile, butyronitrile, benzonitrile and the like. Preparation of the catalyst is not difficult and references to its preparation are found in the literature. For example, the preparation of bis(acetonitrile)chloronitropalladium (II) is given by M. A. Andrews and K. P. Kelly, J. American Chemical Society, 103, 2894 (1981).

The process of this invention is carried out in solvents that will dissolve the olefin, the catalyst and the metallocycle. The solvents are organic aprotic solvents. Suitable solvents can readily be determined from knowledge of the solubilities of the reactants or readily determined by routine experimentation. Suitable solvents include benzene, toluene, xylene, chloroform, tetrahydrofuran, sulfolane, acetone, methylethylketone, methyl acetate, ethyl acetate and the like. The choice of solvent is not critical, but functionally it must be capable of dissolving in part the reactants.

Reaction conditions are not critical and are adjusted according to the particular reactants involved. Generally, temperatures should not be too high or by-products will form and selectivity to β-lactone will decrease. Temperatures ranging from about −50° C. to about 50° C. are suitable. Room temperature is generally suitable. Pressures are not critical and generally are around atmospheric although higher pressures, say 100 atmospheres, are suitable.

The process of the instant invention will be further described by the following illustrative embodiments which are provided for illustration and are not to be construed as limiting the invention.

ILLUSTRATIVE EMBODIMENTS

I. The following example describes the preparation of the catalyst, the reaction of the catalyst with norbornene to produce the metallocycle, carbonylation of the metallocycle with carbon monoxide to produce the β-lactone of 2-exo-hydroxybicyclo[2.2.1]heptane-3-exo-carboxylic acid and $[Pd(NO)Cl]_n$. $[Pd(NO)Cl]_n$ was oxidized to $(CH_3CN)_2$-$PdCl(NO_2)$ to demonstrate the complete redox cycle.

Bis(acetonitrile)chloronitropalladium (II)

A mixture of 9.75 g (55 mmol) of $PdCl_2$ and 500 ml of $CH_3CN$ was stirred overnight at room temperature. To the resulting suspension of $(CH_3CN)_2PdCl_2$ was added 8.46 g (55 mmol) of $AgNO_2$ powder. After stirring for 3 hrs at room temperature, the mixture was filtered to remove precipitated AgCl and the AgCl cake was washed with $CH_3CN$. The orange filtrate was evaporated under reduced pressure to give 14.3 g (53 mmol, 96% yield) of bis(acetonitrile)chloronitropalladium (II) as a yellow-orange powder. (Andrews & Kelly, *J. Am. Chem. Soc.*, 103, 2894 (1981)).

Di-μ-chlorobis[3-(nitrosooxy)-2-norbornyl-C-N]dipalladium (metallocycle)

Norbornene (0.6 g, 6.38 mmol) was added to a solution of bis(acetonitrile)chloronitropalladium (II) (1.55 g, 5.55 mmol) in 75 ml of acetone. After stirring at room temperature for 10 min., the yellow precipitate was isolated by filtration, washed with acetone, and dried under vacuum to give 0.55 g (0.98 mmol, 35% yield) of the metallocycle as a light yellow powder. (Andrews and Cheng, *J. Am. Chem. Soc.*, 104, 4268 (1982)).

Carbonylation of Metallocycle

A solution of 1.2 g (2.13 mmol) of the above prepared metallocycle in 50 ml of chloroform was stirred at room temperature under 1 atm of CO for 90 min. The resulting suspension was filtered and the filter cake was washed with chloroform and dried under vacuum to give 0.62 g (3.6 mmol, 85% yield) of a red-brown powder which was shown to be $[Pd(NO)Cl]_n$ by IR. The pale yellow filtrate was concentrated under reduced pressure. Flash vacuum distillation of the residue gave 0.46 g (3.33 mmol, 78% yield) of the β-lactone as a white solid which was identified by IR spectroscopy, J - Modulated Spin Echo $^{13}C$ NMR Spectroscopy & $^1H$ NMR Spectroscopy as the β-lactone of 2-exo-hydroxybicyclo[2.2.1]heptane-3-exo-carboxylic acid.

Oxidation of Recovered $[Pd(NO)Cl]_n$ to $(CH_3CN)_2PdCl(NO_2)$

A mixture of 0.544 g (3.16 mmol) of $[Pd(NO)Cl]_n$ recovered from the carbonylation of metallocycle, 20 ml of $CH_3CN$ and 80 ml of toluene was stirred at room temperature in air for two days. The resulting suspension was filtered through a fine fritted glass funnel and the filter cake was washed repeatedly with $CH_3CN$ until the washing was colorless. The filtrates were combined and evaporated under reduced pressure to give 0.8 g (2.96 mmol, 94%) of bis(acetonitrile)chloronitropalladium (II) as a yellow-orange powder whose IR spectrum was identical to that of the starting catalyst.

II. The following example describes the conversion of norbornene to the corresponding β-lactone wherein the catalyst, the norbornene and the carbon monoxide are initially combined together.

A mixture of $[(CH_3CN)_2Pd(NO_2)Cl]$ (480 mg, 1.78 mmol), norbornene (1 ml) and toluene (25 ml) was stirred at room temperature under 1 atm of CO for 60 min. Vpc analysis of the liquid phase showed the formation of the exo β-lactone of norbornene (1.66 mmol, 93% yield based on Pd).

III. The following example describes the conversion of isobutylene to the metallocycle, and the subsequent carbonylation of the metallocycle to produce 3,3-dimethylpropiolactone.

The metallocycle adduct of isobutylene and $[(CH_3CN)_2Pd(NO_2)Cl]$ was formed by exposing a solution of $[(CH_2CN)_2Pd(NO_2)Cl]$ in chloroform to 1 atm of isobutylene at room temperature for 1 h (Andrews and Kelly, *J. Am. Chem. Soc.*, 103, 2894 (1981)). Subsequent exposure to 1 atm of CO at room temperature for 60 min. converted the metallocycle to β,β-dimethyl β-propiolactone whose structure was confirmed by IR and NMR.

We claim:

1. A process for converting an olefin selected from the group consisting of norbornene and isobutylene to the corresponding beta-lactone which comprises:
   (a) reacting the olefin with bis(organonitrile)chloronitropalladium (II) in an organic aprotic solvent to form a metallocycle and
   (b) reacting the metallocycle with carbon monoxide in an organic aprotic solvent to produce the beta-lactone.

2. The process of claim 5 wherein the reaction temperature range from −50° C. to about 50° C.

* * * * *